(12) United States Patent
Talamonti

(10) Patent No.: US 7,066,917 B2
(45) Date of Patent: Jun. 27, 2006

(54) ORAL GASTRIC LAVAGE KIT WITH MATCHED ASPIRATION STREAM APERTURES

(76) Inventor: Anthony R. Talamonti, 1710-41 Ave., Kenosha, WI (US) 53144

( * ) Notice: Subject to any disclaimer, the term of this patent is extended or adjusted under 35 U.S.C. 154(b) by 0 days.

(21) Appl. No.: 10/265,550

(22) Filed: Oct. 4, 2002

(65) Prior Publication Data

US 2003/0069553 A1 Apr. 10, 2003

Related U.S. Application Data

(60) Provisional application No. 60/327,445, filed on Oct. 5, 2001.

(51) Int. Cl.
*A61M 1/00* (2006.01)
*A61M 31/00* (2006.01)

(52) U.S. Cl. .......................... 604/320; 604/276; 604/902

(58) Field of Classification Search ................ 604/317, 604/320, 264, 268, 275, 276, 537, 902
See application file for complete search history.

(56) References Cited

U.S. PATENT DOCUMENTS

| | | | | |
|---|---|---|---|---|
| 4,525,156 A | * | 6/1985 | Benusa et al. ................ 604/28 |
| 5,419,769 A | * | 5/1995 | Devlin et al. ................ 604/119 |
| 5,447,494 A | * | 9/1995 | Dorsey, III ................... 604/43 |
| 5,556,390 A | | 9/1996 | Hicks | |
| 5,667,500 A | | 9/1997 | Palmer et al. | |
| 5,776,119 A | * | 7/1998 | Bilbo et al. .................. 604/317 |
| 5,827,218 A | * | 10/1998 | Nguyen et al. ................ 604/30 |
| 5,843,028 A | | 12/1998 | Weaver et al. | |
| 5,890,516 A | | 4/1999 | Talamonti | |
| 5,921,970 A | * | 7/1999 | Vandenberg ................. 604/264 |
| 5,931,831 A | | 8/1999 | Linder | |
| 6,152,886 A | * | 11/2000 | Phelan ........................ 600/571 |
| 6,235,009 B1 | * | 5/2001 | Skow .......................... 604/317 |
| 6,585,708 B1 | * | 7/2003 | Maaskamp ................... 604/317 |
| 2003/0191453 A1 | * | 10/2003 | Velez et al. .................. 604/537 |

OTHER PUBLICATIONS

"Lavacuator Gastro Intestinal Tube", Mallingkrodt Product Catalog, Jun. 6, 2001, Admitted Prior Art.

Ethox Corp. Product Catalog, Admitted Prior Art.

* cited by examiner

*Primary Examiner*—Larry I. Schwartz
*Assistant Examiner*—Michael G. Bogart
(74) *Attorney, Agent, or Firm*—Quarles & Brady LLP

(57) ABSTRACT

A kit includes all the materials necessary for oral gastric lavage in a single pouch. The components, many of which are common hospital supplies, may thus be pre-selected to work together in critical applications and to resist clogging.

11 Claims, 1 Drawing Sheet

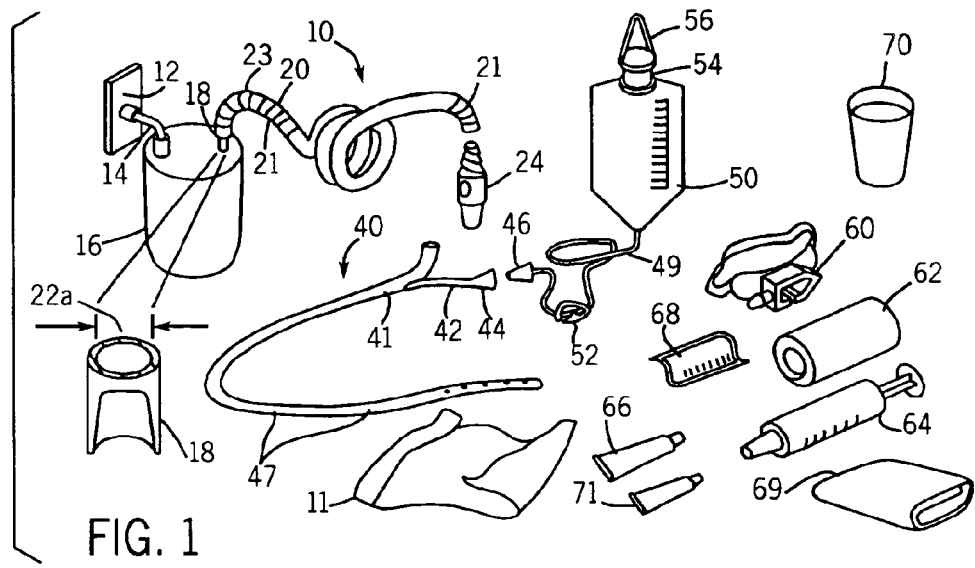
FIG. 1
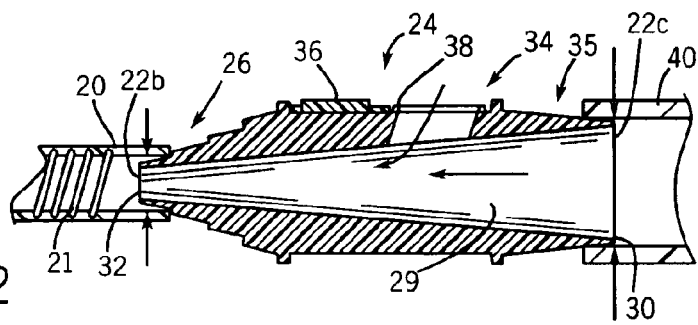
FIG. 2
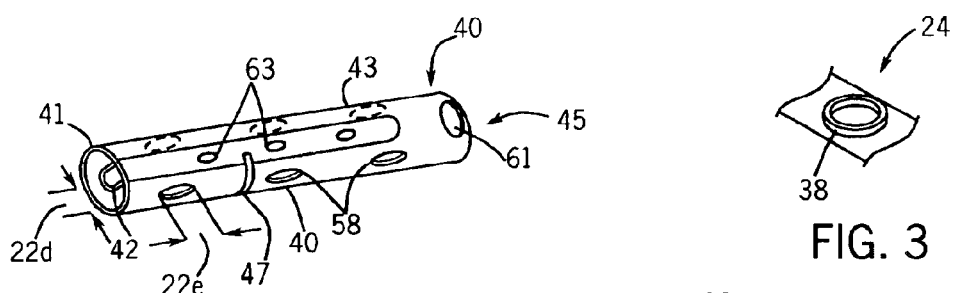
FIG. 3
FIG. 4
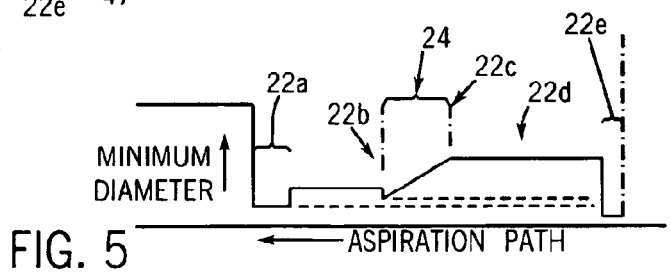
FIG. 5

ORAL GASTRIC LAVAGE KIT WITH MATCHED ASPIRATION STREAM APERTURES

CROSS-REFERENCE TO RELATED APPLICATIONS

This application is based on provisional application No. 60/327,445 filed Oct. 5, 2001 and entitled "Oral Gastric lavage Kit With Matched Aspiration Stream Apertures" and claims the benefit thereof.

STATEMENT REGARDING FEDERALLY SPONSORED RESEARCH OR DEVELOPMENT

Field of the Invention

The present invention relates to a medical lavage apparatus and more particularly to an apparatus used for oral gastric lavage.

BACKGROUND OF THE INVENTION

Acute poisoning is a common cause of morbidity and mortality in children and adults. However, if ingested poison can be removed from the gastrointestinal track before being absorbed, the risk of severe poisoning is reduced. One method of removing ingested poison is that of oral gastric lavage in which the gastrointestinal track or stomach is successively irrigated and aspirated through a lavage tube inserted along the patient's gastrointestinal track to the stomach.

A common method of oral gastric lavage is described in U.S. Pat. No. 5,667,500 which uses parallel connected syringe cylinders having plungers and valves to allow both irrigation and aspiration through a single nozzle connected to a single lumen pliable lavage tube. Such a system requires continual, manual pumping by an attendant.

An improvement is taught in U.S. Pat. No. 5,890,516 which provides an aspiration valve allowing the use of an in-wall vacuum system, such as is commonly found in hospitals, for operation of the lavage system without manual pumping. In this device, a double lumen flexible tube is provided, one lumen delivering an irrigation liquid and the second being used for aspiration through the in-wall vacuum system. The aspiration valve allows continual adjustment of the aspiration pressure.

A problem plaguing all oral gastric lavage systems is clogging of the lavage apparatus, for example, from pill fragments contained in the patient's stomach. A number of methods have been used to attempt to reduce this problem. The above referenced U.S. Pat. No. 5,667,500 describes the use of special, large size, slit valves and back flushing of the lumen tube with irrigant, a procedure not available with the more convenient dual lumen design. U.S. Pat. No. 5,890,516 provides the aspiration valve with a funnel-shaped connector tapering smoothly to a sharp lip to reduce the possibility of particles becoming lodged at the interface between the aspiration valve and a dual lumen lavage tube.

These solutions are not wholly satisfactory and clogging of lavage systems is still common.

BRIEF SUMMARY OF THE INVENTION

The present inventors have recognized that clogging, particularly in the dual lumen design, can be significantly reduced by matching the components together in a single kit. Key to the matching is that the diameter of connections of all successive portions of the aspiration path from the distal portion of the lavage tube to the inlet to the collection vessel attached to the in-wall vacuum system must be greater than or equal to the diameter of the initial inlet apertures of the distal portion of the lavage tube. The potential for clogging may be thereby moved to the interface between the distal portion of the lavage tube and the stomach where the inventors believe that the multiple apertures, better accommodate some clogging without significant effect, and where clogging fragments may be more easily dislodged with the cessation of aspiration pressure. The inventors have further recognized that in the real world hospital environment, proper operation of the oral gastric lavage system requires that the components of the system be pre-collected in a single location and pre-selected to work together. Accordingly a kit containing all the components necessary for oral gastric lavage in a single package is highly desirable, even though many of the components are multi-use products generally available in a hospital environment and could be obtained if not in such a kit.

BRIEF DESCRIPTION OF THE DRAWINGS

FIG. 1 is a perspective view of components of the oral gastric lavage kit of the present invention showing the in-wall vacuum system and its collection vessel, the aspiration valve, the dual lumen lavage tube, the irrigation bag, and other components;

FIG. 2 is a cross-sectional view of the aspiration valve showing the key internal diameters;

FIG. 3 is a fragmentary perspective view of the aspiration valve of FIG. 1 showing the introduction of an improved sealing ridge around the bleed air inlet;

FIG. 4 is a fragmentary view of the distal end of the dual lumen lavage tube showing its key dimensions; and FIG. 5 is a plot of internal diameters plotted against distance along the aspiration path of the kit of FIG. 1.

DETAILED DESCRIPTION OF THE PREFERRED EMBODIMENT

Referring now to FIG. 1, an oral gastric lavage kit 10 of the present invention, such as may be collected and sealed in a plastic pouch 11, is adapted for use with an in-line vacuum system 12 providing a vacuum line 14 received by a collection vessel 16 to draw air therefrom.

The collection vessel 16 serves as a trap for receiving solids and liquids drawn through inlet 18, the latter which may be connected to vacuum tube 20 to provide a flexible source of suction for hospital procedures. The inlet 18 provides the last restriction through which material collected from the gastrointestinal track must pass before reaching the collection vessel 16 and present an opening size 22*a* that remains relatively standard from hospital to hospital.

In an alternative embodiment (not shown), the kit 10 includes a collapsible collection vessel that may be attached upstream of the vacuum tube 20 to reduce the transport distances required of pumped material. In this case, collection vessel 16 is not required and vacuum tube 20 is attached directly to the in-line vacuum system 12.

The vacuum tube 20 will have an internal diameter of greater than this opening size 22*a* of the inlet 18 as it fits over the outside of the inlet 18. The present invention provides a kit including this vacuum tube 20 and additional components as will be described. The vacuum tube 20 may include a vortex device 21 (shown in FIG. 1) such as a "corkscrew" spiral made by an internal groove causing a vortex flow of liquid in the vacuum tube 20 placed near the inlet 18. The vortex device improves the flow of air and liquid. On the distal end of the vacuum tube 20, a corrugated elbow 23 is used to prevent kinking.

Referring now also to FIG. 2, the oral gastric lavage kit 10 further includes an aspiration valve 24 providing for upstream control of the pressure of the vacuum to an amount less than that present at the vacuum tube 20. Generally, the aspiration valve 24 provides a step-tapered end 26 receiving the vacuum tube 20 by interference fit of the inner diameter of the vacuum tube 20 against an outer ridged surface of the step-tapered end 26. The aspiration valve 24 provides a conically expanding central channel through the aspiration valve 24 to an opposite flare end 35 which may receive the oral gastric lavage tube 40. Notably, the flare end 35 of the aspiration valve 24 opposite the step tapered end 26 provides for a thin lip 30 that may fit snugly against the inside of the oral gastric lavage tube 40 to provide a relatively smooth inner wall transition from oral gastric lavage tube 40 to the inner passage 29 thus minimizing the change of particles and the like catching and clogging the pathway. The principal features of this valve are described in U.S. Pat. No. 5,890,516, hereby incorporated by reference.

The opening size 22b of the step tapered end 26 and the opening size 22c of the flare end 35 of the aspiration valve 24 are selected to be no smaller than the size 22e of the distal portion of the oral gastric lavage tube 40 as will be described below.

The aspiration valve 24 includes a bleed-air inlet 34 allowing ingress of air to reduce the suction drawn on the oral gastric lavage tube 40. Air flow through the bleed-air inlet 34 may be controlled by sliding inlet cover 36 which may be moved to variably occlude the bleed air inlet port 34.

Referring to FIG. 3, the valve described in the aforementioned '516 patent is modified over that description by the introduction of a sealing ridge 38 around the bleed-air inlet 34 providing improved sealing and retention of the sliding inlet cover 36.

Referring now to FIGS. 1 and 4, the oral gastric lavage tube 40 may be a coaxial tube including an outer lumen 41 for aspiration and an inner lumen 42 for irrigation. Dual lumen gastrointestinal tubes may be obtained from Mallinckrodt under the trade name Lavacuator gastrointestinal tube and are available in sizes 18, 22, 28, 32, and 36 French and in length 48 inches. Preferably, however, the oral gastric lavage tube 40 would have an inner diameter of 34 French. The oral gastric lavage tube 40 may include a radio opaque stripe 43 to assist in location of the tube under fluoroscopic examination and may include graduations 47 in centimeters together with centimeter numbers to assist the attending physician in placement of the oral gastric lavage tube 40 in the gastrointestinal tract.

The inner lumen 42 may terminate at a proximal end with a funnel connector 44 to be received by corresponding cone connector 46 of connector line 49 of a 3500 cc irrigation bag 50. The connector line may include a ratchet clamp 52 for metering the irrigant flow. The irrigation bag 50 provides a cap 54 and hanger 56 for suspension on an IV pole according to techniques well known in the art.

Referring to FIG. 4, the outer lavage tube includes a number of eye holes 58 at its distal end 45. The inner lumen 42 which is adhered to one wall of the outer lumen 41 is terminated at the distal end 45 and has much smaller eye holes 63 for providing irrigation fluid from the irrigation bag 50.

Referring to FIGS. 1 and 5, the eye holes 58 are elliptical in shape and have size 22e less than the sizes 22a–22d as measured by the minor diameter of the ellipse of the eye holes 58 and preferably a size of 20 French. An open end 61 of the oral gastric lavage tube 40 may be sealed or may be left open provided its diameter is less than sizes 22a–22d as described above. By incorporating the vacuum tube 20, the aspiration valve 24, and oral gastric lavage tube 40 into one kit, the relative sizes of the eye holes 58 and of all intervening restrictions 22a–22d may be controlled so as to significantly reduce clogging in a dual lumen system.

As a matter of convenience, the oral gastric lavage kit 10 may also include other convenient elements including a bite block 60 of the style that is commercially available in the art, a biohazard bag 62 for disposal of the lavage kit when complete, a 140 cc syringe 64 with a 34 French tip for introducing the charcoal suspension and injecting air into the lavage tube 40 for placement verification with a stethoscope. The irrigation bag 50 and its associated parts are included to ensure compatibility with the desired oral gastric lavage tube 40. The kit may also include a lubricant 68 for lubricating the oral gastric lavage tube 40 for insertion into the GI track. Alternatively, the oral gastric lavage tube 40 may be pre-coated with a commercially available hydrophilic coating that becomes lubricious when made wet such as is manufactured by Hydromer of Somerville, N.J. and others.

Other elements of the oral gastric lavage kit 10 may include a container of activated charcoal suspension 66 such as is commercially available, sorbitol 71, a disposable gown 69, and an emesis bag 70. Separate sorbitol and charcoal containers are provided to allow the attending physician to elect not to use the sorbitol while still using the charcoal.

I claim:

1. A kit for oral gastric lavage comprising:
   a dual lumen catheter having an in-patient end perforated with a plurality of catheter openings having catheter opening sizes;
   an aspiration valve fitting at an out-patient end of the dual lumen catheter for moderating the vacuum on the catheter, the aspiration valve having a valve opening size;
   a collection vessel attachable to the aspiration valve and having an inlet port having a port opening size;
   wherein the catheter opening size is selected to be no greater than the valve opening size and the port opening size; and
   wherein the vacuum tube includes a corkscrew spiral causing a vortex flow in the vacuum tube.

2. A kit for oral gastric lavage comprising:
   a dual lumen catheter having an in-patient end perforated with a plurality of catheter openings having catheter opening sizes;
   an aspiration valve fitting at an out-patient end of the dual lumen catheter for moderating the vacuum on the catheter, the aspiration valve having a valve opening size;
   a collection vessel attachable to the aspiration valve and having an inlet port having a port opening size;
   wherein the catheter opening size is selected to be no greater than the valve opening size and the port opening size; and
   wherein the dual catheter includes a radio opaque marker.

3. A kit for oral gastric lavage comprising:
   a dual lumen catheter having an in-patient end perforated with a plurality of catheter openings having catheter opening sizes;
   an aspiration valve fitting at an out-patient end of the dual lumen catheter for moderating the vacuum on the catheter, the aspiration valve having a valve opening size;

a collection vessel attachable to the aspiration valve and having an inlet port having a port opening size;

wherein the catheter opening size is selected to be no greater than the valve opening size and the port opening size; and wherein the kit further includes a lavage bag holding a lavage liquid and having a connector attaching to one lumen of the dual lumen catheter.

4. The kit for oral gastric lavage recited in claim 3 wherein the kit further includes a bit block fitting around the catheter for gripping by a patients teeth.

5. The kit for oral gastric lavage recited in claim 3 wherein the kit further includes lubricant for the catheter.

6. The kit for oral gastric lavage recited in claim 3 wherein the kit further includes a syringe releasably interfitting with the catheter for the injection of materials therein.

7. The kit for oral gastric lavage recited in claim 3 wherein the kit further includes a container of activated charcoal.

8. The kit for oral gastric lavage recited in claim 3 wherein the kit further includes a container of sorbital.

9. The kit for oral gastric lavage recited in claim 3 wherein the kit further includes a disposable gown.

10. The kit for oral gastric lavage recited in claim 3 wherein the kit further includes an emesis bag.

11. The kit for oral gastric lavage recited in claim 3 wherein the aspiration valve includes a bleed-air inlet allowing ingress of air to reduce the vacuum applied to the catheter, the bleed-air inlet variably covered by a sliding inlet cover sliding on a sealing ridge around the bleed-air inlet.

\* \* \* \* \*

UNITED STATES PATENT AND TRADEMARK OFFICE
CERTIFICATE OF CORRECTION

| | | |
|---|---|---|
| PATENT NO. | : 7,066,917 B2 | Page 1 of 1 |
| APPLICATION NO. | : 10/265550 | |
| DATED | : June 27, 2006 | |
| INVENTOR(S) | : Anthony R. Talamonti | |

It is certified that error appears in the above-identified patent and that said Letters Patent is hereby corrected as shown below:

In column 4, line 60, after "dual" insert --lumen--.

Signed and Sealed this

Twelfth Day of September, 2006

JON W. DUDAS
*Director of the United States Patent and Trademark Office*